(12) United States Patent
Kim et al.

(10) Patent No.: US 9,229,096 B2
(45) Date of Patent: Jan. 5, 2016

(54) TIME-OF-FLIGHT IMAGING SYSTEMS

(75) Inventors: Dongsoo Kim, San Jose, CA (US); Jae Eun Lim, Boise, ID (US); Kwangbo Cho, San Jose, CA (US)

(73) Assignee: Semiconductor Components Industries, LLC, Phoenix, AZ (US)

(*) Notice: Subject to any disclaimer, the term of this patent is extended or adjusted under 35 U.S.C. 154(b) by 1030 days.

(21) Appl. No.: 13/278,019

(22) Filed: Oct. 20, 2011

(65) Prior Publication Data

US 2013/0026384 A1 Jan. 31, 2013

Related U.S. Application Data

(60) Provisional application No. 61/512,306, filed on Jul. 27, 2011.

(51) Int. Cl.

| | | |
|---|---|---|
| *H01L 31/16* | (2006.01) | |
| *G01S 7/486* | (2006.01) | |
| *H04N 5/225* | (2006.01) | |
| *H04N 5/232* | (2006.01) | |
| *G01S 17/89* | (2006.01) | |
| *G01J 1/42* | (2006.01) | |
| *G01J 1/44* | (2006.01) | |
| *H01L 27/148* | (2006.01) | |
| *H04N 5/359* | (2011.01) | |
| *H04N 5/3745* | (2011.01) | |
| *H04N 13/02* | (2006.01) | |

(52) U.S. Cl.

CPC .............. *G01S 7/4863* (2013.01); *G01S 17/89* (2013.01); *H01L 31/165* (2013.01); *H04N 5/2258* (2013.01); *H04N 5/2327* (2013.01); *G01J 2001/4238* (2013.01); *G01J 2001/444* (2013.01); *G01N 2201/0696* (2013.01); *H01L 27/148* (2013.01); *H04N 5/359* (2013.01); *H04N 5/37452* (2013.01); *H04N 13/0253* (2013.01)

(58) Field of Classification Search

CPC . H01L 31/16; H01L 27/148; G01J 2001/444; G01C 3/08; H04N 5/37452; H04N 5/2256; H04N 5/272; H04N 5/341
USPC ........... 250/370.01, 370.14, 393; 348/49, 371
See application file for complete search history.

(56) References Cited

U.S. PATENT DOCUMENTS

2008/0231737 A1* 9/2008 Weale et al. .................. 348/308

OTHER PUBLICATIONS

Lange et al., "Solid-State Time-of-Flight Range Camera", IEEE Journal of Quantum Electronics, vol. 37, No. 3, Mar. 2001.
Magnan, "3D Time-Of-Flight Image Capture with Pulsed Illumination", IEEE International Solid-State Circuits Conference Session F5: Image Sensors for 3d capture, Feb. 24, 2011, San Francisco, CA.

* cited by examiner

*Primary Examiner* — David Porta
*Assistant Examiner* — Carolyn Igyarto
(74) *Attorney, Agent, or Firm* — Treyz Law Group; Kendall P. Woodruff

(57) ABSTRACT

Electronic devices may include time-of-flight image pixels. A time-of-flight image pixel may include first and second charge storage regions coupled to a photosensor and a transfer transistor with a gate terminal coupled to the first storage region. An electronic device may further include a light pulse emitter configured to emit pulses of light to be reflected by objects in a scene. Reflected portions of the emitted pulses of light may be captured along with background light by the time-of-flight image pixels. Time-of-flight image pixels may be configured sense the time-of-flight of the reflected portions of the emitted pulses. The electronic device may include processing circuitry configured to use the sensed time-of-flight of the reflected portions to generate depth images of a scene. Depth images may include depth-image pixel values that contain information corresponding to the distance of the objects in the scene from the electronic device.

13 Claims, 12 Drawing Sheets

TIME-OF-FLIGHT IMAGING SYSTEMS

This application claims the benefit of provisional patent application No. 61/512,306, filed Jul. 27, 2011, which is hereby incorporated by reference herein in its entirety.

BACKGROUND

This relates generally to imaging devices, and more particularly, to imaging devices that measure the flight time of reflected light pulses.

Image sensors are commonly used in electronic devices such as cellular telephones, cameras, and computers to capture images. In a typical arrangement, an electronic device is provided with an image sensor and a corresponding lens. Some electronic devices use arrays of image sensors and corresponding lenses to gather image data. This type of system, which is sometimes referred to as an array camera, may be used to capture depth information from a scene using a parallax effect based on a known physical offset between image sensors.

Depth information such as information about the distance of an object from an electronic device is also commonly captured using a dedicated range finder such as a radar system. In a typical range finder, light of a known frequency is emitted from the range finder in the direction of an object and is reflected off of the object in the direction of the range finder. Range finders typically have a light sensor that detects the reflected light. Distance information is then determined based on the time-of-flight of the light between the emission and detection of the light and the known speed of light.

Time-of-flight distance information is also sometimes extracted by a range finder from an emitted and reflected pulse of light by synchronizing the emission and the detection of the light. The light sensor is often configured to collect light for a predetermined amount of time after the emission of the light. Light reflected from a far away object may not return during the light collection period while light reflected from a nearby object may return and be collected during the light collection period. This is because the light reflected from the far away object travels a longer distance and therefore has a longer time-of-flight. Closer objects therefore appear brighter than relatively further objects. Distance information is therefore extracted from the brightness of an object.

Range finding systems of this type may capture depth information to a relatively larger distance than can be determined using a typical array camera. However, range finding systems of this type typically collect distance information for a single point, not a collection of points as in an image. In addition, range finding systems that determine depth information based on the brightness of reflected light may be confused by the presence of differences in the intrinsic brightness of objects in a typical real-world scene. Difficulties that arise in separating background intensity from reflected light pulse intensity can therefore be problematic when capturing images with depth information.

It would therefore be desirable to be able to provide improved imaging devices for capturing depth images.

BRIEF SUMMARY OF THE INVENTION

Various embodiments are described, illustrating electronic devices that include time-of-flight image pixels configured to measure the time of flight of an emitted light pulse for sensing distance information about objects in a scene. Emitted light pulses may be generated by a light pulse emitter on the electronic device and reflected from objects in the field-of-view of the time-of-flight image pixels. Time-of-flight image pixels may be configured to measure differences in time-of-flight between reflected portions of emitted light pulses using differences in brightness of the reflected portions. Time-of-flight image sensors may be configured to remove background light contamination of reflected portions of emitted light pulses.

A time-of-flight image pixel may include a photosensitive element such as a photodiode, and first and second charge storage regions coupled to the photosensitive element. A time-of-flight image pixel may include a first transfer transistor coupled between the photosensitive element and the first charge storage region and a second transfer transistor coupled between the photosensitive element and the second charge storage region. The second transfer transistor may include a gate terminal that is coupled to the first charge storage region.

A time-of-flight image pixel may include a third transfer transistor having first and second source/drain terminals. The first source/drain terminal of the third transfer transistor may be connected to the gate terminal of the second transfer transistor and the second source/drain terminal of the third transfer transistor may be connected to the first charge storage region.

A time-of-flight image pixel may include a fourth transfer transistor having a first source/drain terminal that is coupled to the gate terminal of the second transfer transistor and a reset transistor having a first source/drain terminal that is coupled to the second charge storage region and a second source/drain terminal coupled to a source/drain terminal of a source follower transistor having a gate terminal connected to the second charge storage region. If desired, a time-of-flight image pixel may include an additional reset transistor having a first source/drain terminal that is coupled to the photosensitive element.

If desired, the time-of-flight image pixel may include a reset transistor having a first source/drain terminal that is coupled to the second charge storage region, a source follower transistor having a gate terminal connected to the second charge storage region, and a row select transistor coupled to the source follower transistor.

The electronic device may further include a light pulse emission component such as a non-visible light pulse emitter configured to emit pulses of non-visible light. The electronic device may include an array of image sensors. The array of image sensors may include a red image sensor, a blue image sensor, a green image sensor or other image sensors. Each of the image sensors in the array of image sensors may include an array of time-of-flight image pixels. Time-of-flight image pixels may be configured to collect background light and reflected portions of the emitted pulses of non-visible light and to store charges generated by the background light on the first charge storage region and to store charges generated by the reflected portions of the emitted pulses of non-visible light on the second charge storage region.

The electronic device may include processing circuitry configured to extract depth information from a depth-image signal generated by the time-of-flight image pixels. The processing circuitry may be configured to combine image data from the red image sensor, the blue image sensor, and the green image sensor to form a color image.

During operation of the electronic device, time-of-flight image pixels may be configured to convert background light into electric charges and to transfer the electric charges from the photosensitive element to the first charge storage region. A light pulse emitter may be configured to emit a pulse of non-visible light. Time-of-flight image pixels may be configured to convert additional background light and a reflected portion of the emitted pulse of non-visible light into additional electric charges and to transfer a portion of the additional electric charges (e.g., the portion corresponding to the reflected portion of the emitted pulse of non-visible light) to the second charge storage region. Transferring the portion of the additional electric charges may include connecting the gate terminal of the second transfer transistor to the first charge storage region on which the electric charges are stored by activating the fourth transfer transistor.

During operation, the photosensitive element may be reset to remove a remaining portion of the additional electric charges from the photosensitive element before a subsequent pulse of non-visible light may be emitted from the light pulse emitter. Time-of-flight image pixels may be configured to convert further additional background light and a reflected portion of the subsequent emitted pulse of non-visible light into further additional electric charges and to transfer a portion of the further additional electric charges (e.g., the portion corresponding to the reflected portion of the subsequent emitted pulse of non-visible light) to the second charge storage region on which the portion of the additional electric charges is stored.

Time-of-flight image pixels may be configured to convert the portion of the additional electric charges and the portion of the further additional electric charges into a depth-image signal. Processing circuitry may be used to extract distance information from the depth-image signal and to process the distance information to form a portion of a depth image that includes depth-image pixel values that correspond to the distance of an object to the electronic device.

DETAILED DESCRIPTION

Digital camera modules are widely used in electronic devices such as digital cameras, computers, cellular telephones, or other electronic devices. These electronic devices may include image sensors that gather incoming light to capture an image. The image sensors may include arrays of image pixels. The image sensors may include arrays of time-of-flight image pixels for sensing the flight time of a light pulse emitted by a non-visible-light emitting component of the electronic device and reflected from an object. Image sensors may, if desired, include both image pixels and time-of-flight image pixels. Image pixels and time-of-flight image pixels in the image sensors may include photosensitive elements such as photodiodes that convert the incoming light into electric charges.

Time-of-flight image sensor pixels may include one or more charge storage regions for storing charges collected using photosensitive elements. Time-of-flight image sensors may be configured to store charges generated by background image light from a scene separately from charges generated by reflected light that was emitted by a non-visible-light emitting component of the electronic device. Charges generated by reflected light that was emitted by a non-visible-light emitting component of an electronic device may be converted into depth-image data. The depth-image data may be processed to form depth images (i.e., images in which the image data in each pixel of the image represents the distance to the object in that pixel). Image sensors may have any number of pixels such as image pixels and/or time-of-flight image pixels (e.g., hundreds or thousands or more). A typical image sensor may, for example, have hundreds of thousands or millions of pixels (e.g., megapixels).

Figure 1:
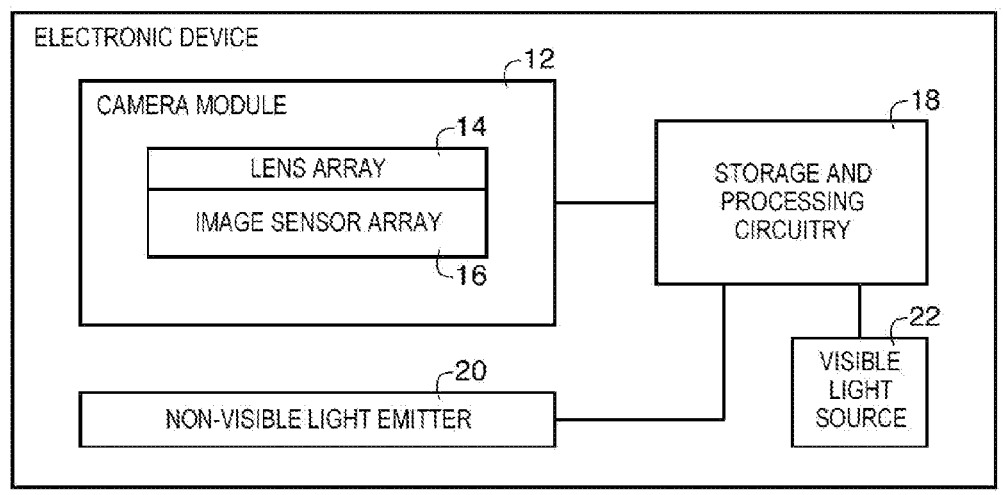
FIG. 1 is a diagram of an illustrative electronic device in accordance with an embodiment of the present invention.

FIG. 1 is a diagram of an illustrative electronic device that includes time-of-flight image pixels and a light pulse emitter for capturing depth images. Electronic device 10 of FIG. 1 may be a portable electronic device such as a camera, a cellular telephone, a video camera, or other imaging device that captures digital image data. Camera module 12 may be used to convert incoming light into digital image data. Camera module 12 may include an array of lenses 14 and a corresponding array of image sensors 16. Lenses 14 and image sensors 16 may be mounted in a common package and may provide image data to control circuitry such as storage and processing circuitry 18.

Electronic device 10 may include one or more light emitting components such as visible light source 22 (e.g., a camera flash, an LED light source, etc.) and a non-visible-light pulse emitter (e.g., an infrared laser, a radio pulse emitter, or other source non-visible light capable of generating pulses of non-visible light) such as non-visible light emitter 20. Visible light source 22 may be used to light a real-world scene during capture of image data. Non-visible-light emitter 20 (sometimes called light pulse emitter, pulse emitter, infrared emitter, emitter, etc.) may be used to emit a pulse of, for example, infrared light. Light emitted by pulse emitter 20 may be reflected off of objects in a real-world scene and detected using image sensor array 16 of camera module 12. Circuitry 18 may be used to extract depth information (e.g., information about the distance of objects in a scene) from detected, reflected portions of light emitted by pulse emitter 20.

Storage and processing circuitry 18 may include one or more integrated circuits (e.g., image processing circuits, microprocessors, storage devices such as random-access memory and non-volatile memory, etc.) and may be implemented using components that are separate from camera module 12 and/or that form part of camera module 12 (e.g., circuits that form part of an integrated circuit that includes image sensors 16 or an integrated circuit within module 12 that is associated with image sensors 16). Image data that has been captured by camera module 12 may be processed and stored using circuitry 18. Processed image data may, if desired, be provided to external equipment (e.g., a computer or other device) using wired and/or wireless communications paths coupled to processing circuitry 18.

Figure 2:
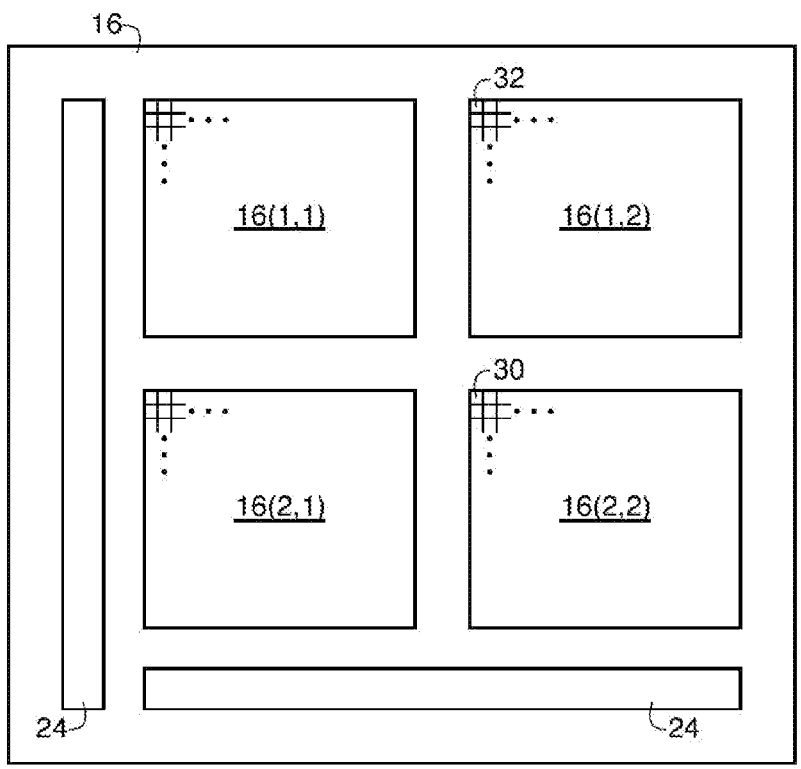
FIG. 2 is a top view of an illustrative image sensor array in accordance with an embodiment of the present invention.

As shown in FIG. 2, image sensor array 16 may contain an array of individual image sensors having image pixels such as image sensor pixels 30. In the example of FIG. 2, image sensor array 16 includes four image sensors 16(1,1), 16(1,2), 16(2,1), and 16(2,2). This is merely illustrative. In general, array 16 may have any suitable number of image sensors (e.g., one image sensor, two or more image sensors, three or more image sensors, four or more image sensors, ten or more sensors, 16 image sensors, 20 or more image sensors, etc.).

Image sensors such as image sensors 16(1,1), 16(1,2), 16(2,1), and 16(2,2) may each be configured to receive light of a given color by providing each image sensor with a color filter. The color filters that are used for image sensor pixel arrays in the image sensors may, for example, be red filters that pass red light, blue filters that pass blue light, green filters that pass green light, and infrared filters that pass infrared light. Each filter may form a color filter layer that covers the image sensor pixel array of a respective image sensor in the array. Other filters such as white color filters, dual-band IR cutoff filters (e.g., filters that allow visible light and a range of infrared light emitted by LED lights), etc. may also be used.

Image sensors such as image sensors 16(1,1), 16(1,2), 16(2,1), and 16(2,2) may be formed on one or more separate semiconductor substrates. With one suitable arrangement, which is sometimes described herein as an example, the image sensors are formed on a common semiconductor substrate (e.g., a common silicon image sensor integrated circuit die). Each image sensor may be identical. For example, each image sensor may be a Video Graphics Array (VGA) sensor with a resolution of 480×640 sensor pixels (as an example). Other types of image sensor may also be used for the image sensors if desired. For example, images sensors with greater than VGA resolution or less than VGA resolution may be used, image sensor arrays in which the image sensors are not all identical may be used, etc.

Image sensors such as image sensors 16(1,1), 16(1,2), 16(2,1), and 16(2,2) of camera module 12 may include one or more time-of-flight image sensors having time-of-flight image pixels such as time-of-flight image pixels 32. A time-of-flight image sensor may be used to capture depth-image light for generating depth information about a real-world scene. Depth-image data may be captured in the form of electric charges generated by photosensors such as photodiodes in time-of-flight image pixels 32. These depth-image charges may be generated by detected portions of light emitted by emitter 20 of FIG. 1 and reflected from objects in a real-world scene.

In one preferred embodiment that is sometimes described herein as an example, light emitted by emitter 20 may include infrared image light and a time-of-flight image sensor may be implemented using an infrared image sensor (e.g., an image sensor with an associated infrared color filter or an image sensor with infrared sensitive time-of-flight image pixels).

Image data such as red image data, blue image data, green image data, time-of-flight image data or other image data may be processed by processing circuitry 18. Time-of-flight image data may be processed by circuitry 18 to extract depth information about a scene from the image data (e.g., the distance of an object imaged by each time-of-flight image pixel 32 in electronic device 10).

Processing circuitry 18 (e.g., processing circuitry integrated onto sensor array integrated circuit 16 and/or processing circuitry on one or more associated integrated circuits) may use the relative brightness of detected, reflected image light to determine the distance to the object in the field-of-view of each time-of-flight image pixel 32. Time-of-flight image pixels 32 in image sensor array 16 may include multiple charge storage regions configured to store charges associated with reflected portions of light that was generated by emitter 20 (see FIG. 1) separately from charges generated by background light.

Processing circuitry 18 (e.g., processing circuitry integrated onto sensor array integrated circuit 16 and/or processing circuitry on one or more associated integrated circuits) may also combine color image data (e.g., red, green, blue or other color image data) with depth-image data to form a three-dimensional color image of a scene. In some modes of operation, all of the image sensors on array 16 may be active (e.g., when determining 3-dimensional image depth information). In other modes of operation (e.g., color imaging), only a subset of the image sensors may be used. Other sensors may be inactivated to conserve power (e.g., their positive power supply voltage terminals may be taken to a ground voltage or other suitable power-down voltage and their control circuits may be inactivated or bypassed).

If desired, camera module 12 may include a single image sensor array with time-of-flight image pixels 32. If desired, camera module 12 may include one or more image sensor arrays each having a mix of conventional image pixels 30 and time-of-flight image pixels 32. However, this is merely illustrative. If desired, each image sensor of image sensor array 16 may include exclusively conventional image pixels 30 or exclusively time-of-flight image pixels 32.

Image sensor array 16 may also include circuitry such as support circuitry 24 (e.g., row select and control driver circuitry). Support circuitry 24 may be used to issue reset signals, row select signals, etc. for the image pixels 30 and time-of-flight image pixels 32 of image sensor pixel arrays such as image sensors 16(1,1), 16(1,2), 16(2,1), and 16(2,2). Support circuitry 24 may likewise be used for reading out image data and depth-image data along output lines associated with image pixels and time-of-flight image pixels respectively.

Figure 3:
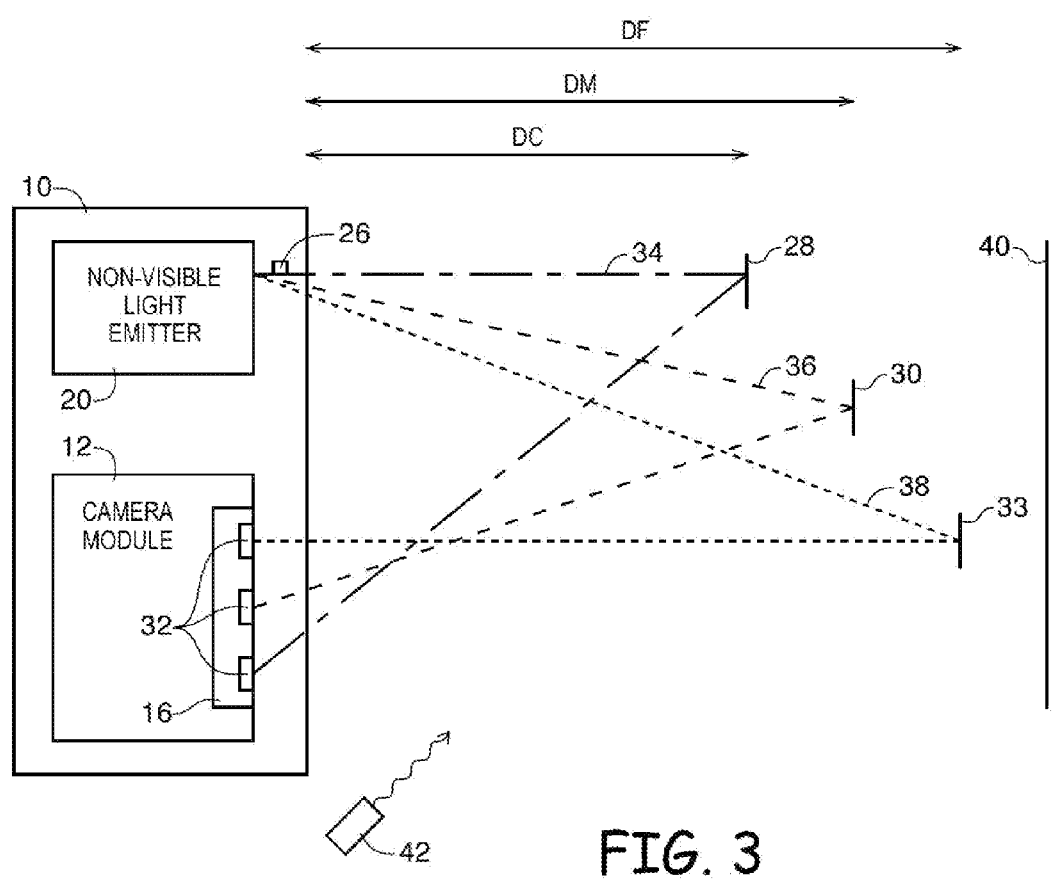
FIG. 3 is a diagram of an illustrative electronic device of the type shown in FIG. 1 showing how light may be reflected from objects at various distances in accordance with an embodiment of the present invention.

Time-of-flight image pixels 32 may be configured to receive light reflected from objects in a real-world scene as shown in FIG. 3. In the example of FIG. 3, a light pulse emitter such as non-visible light emitter 20 may be configured to emit one or more pulses of, for example, infrared light such as pulse 26. Camera module 12 may be configured to receive a portion of light pulse 26 that is reflected from multiple objects such as objects 28, 30, and 33 having distances DC, DM, and DF from electronic device 10 respectively. As shown in FIG. 3, portions of light pulse 26 may travel from emitter 20 to objects 28, 30, and 33 along paths such as paths 34, 36, and 38 respectively.

Because distance DF to object 33 is larger than distances DM and DC to objects 30 and 28 respectively, path 38 may be longer than paths 36 and 34. Because path 34 is longer than paths 36 and 34, the portion of light pulse 26 that is reflected from object 33 will take a longer period of time to reach image sensor array 16 than portions of light pulse reflected from objects 28 and 30. The time-of-flight of returning portions of light pulse 26 may therefore depend on distances such as distances DC, DM, and DF to objects in a real-world scene.

Time-of-flight image pixels 32 may be configured to sense relative differences in the time-of-flight of returning portions of light pulse 26 by sensing how much of returning portions of light pulse 26 return within a predetermined light collection period (sometimes called integration time or exposure time). Time-of-flight image pixels 32 may be configured to sense how much of returning portions of light pulse 26 return within a predetermined light collection period by determining the relative quantity of light sensed by time-of-flight image pixels 32. However, variations in intrinsic brightness of objects in a scene due to variations in object color and illumination may be problematic when extracting information about the how much of returning portions of light pulse 26 return within the predetermined integration time.

For example, a real-world scene may contain other objects such as background object 40 and may be illuminated by light sources other than emitter 20 such as external light source 42. External light source 42 may be the Sun, the Moon, a flame, an indoor or outdoor electric light (e.g., an incandescent or fluorescent) or other light source or combination of light sources. Object 40 may be located behind objects such as objects 28, 30, and 33, in front of objects 28, 30, and 33, may form a portion of objects 28, 30, and 33 or may be otherwise positioned in the field-of-view of camera module 12. Objects 28, 30, 33, and 40 may be uniform in color or may have portions that have different colors from other portions. Objects 28, 30, 33, and 40 may be uniformly illuminated by light sources such as light source 42 or may have portions that are in bright light and portions that are in relative darkness.

Variations in intrinsic brightness of objects 28, 30, 33, and 40 due to variations in color and illumination may cause differences in the quantity of light received by camera module 12 of device 10 that are unrelated to differences in distance (e.g., distances DC, DM, DF, or other object distance). Time-of-flight image pixels 32 may be configured to partially or completely remove intrinsic brightness (e.g., background light) from reflected portions of a light pulse emitted by emitter 20.

The example of FIG. 3 in which device 10 determines distances to three objects is merely illustrative. In general, device 10 may determine distances to a number of objects equal to or less than the number of time-of-flight image pixels (e.g., tens, hundreds, thousands, millions or more) in image sensor array 16. Device 10 may determine relative distances to multiple portions of a single object.

Figure 4:
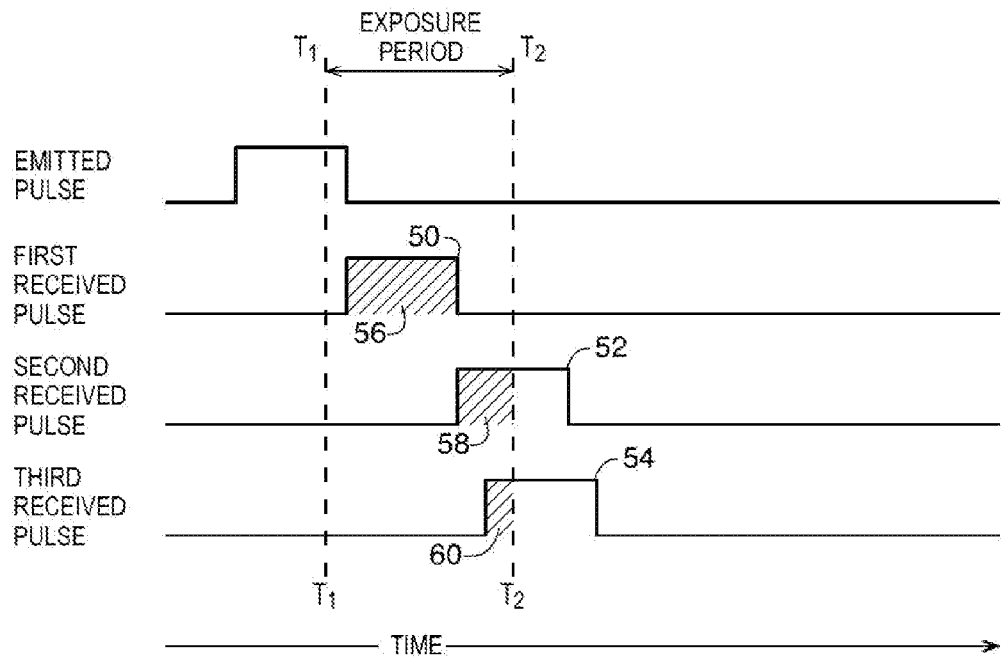
FIG. 4 is an illustrative timing diagram showing how captured light reflected from objects at various distances depends on the object distances in accordance with an embodiment of the present invention.

FIG. 4 is a diagram showing how returning portions of an emitted light pulse that are reflected by objects in a scene may be affected by the distance to a reflecting object. As shown in FIG. 4, an emitted pulse of light such as pulse 26 may be emitted in the direction of objects in a real-world scene. Time-of-flight image pixels 32 may receive returning pulses of reflected light such as returning pulses 50, 52, and 54. Returning pulses 50, 52, and 54 may, for example be returning portions of emitted pulse 26 that have been reflected from objects 28, 30, and 33 of FIG. 3 respectively.

Time-of-flight image pixels 32 may be configured to collect light for an exposure period (e.g., an exposure time, integration time, or light collection period) beginning at time T1 and ending at time T1. In the example of FIG. 4, time T1 occurs after the beginning of pulse 26 and before the end of pulse 26. This is merely illustrative. Pulse 26 may begin and end before time T1 or pulse 26 may begin and end after time T1 and before time T2 if desired.

Because returning pulses 50, 52, and 54 travel along paths 34, 36, and 38 (see FIG. 3), pulse 50 may return to device 10 before pulse 52 and pulse 52 may return to device 10 before pulse 54. Because time-of-flight image pixels 32 collect light for a predetermined light collection period, time-of-flight image pixels 32 may only collect portions of a return pulse that arrive during the exposure period. Therefore, because path 34 is relatively short, portion 56 of return pulse 50 that returns during the exposure period may include substantially all of return pulse 50. Because path 36 is relatively longer than path 34, only a fractional portion such as portion 58 of return pulse 52 may be detected by a time-of-flight pixel 32 during the exposure period. Similarly, because path 38 is relatively long, a relatively smaller fractional portion 60 of return pulse 52 may be detected by a time-of-flight pixel 32 during the exposure period.

Figure 5:
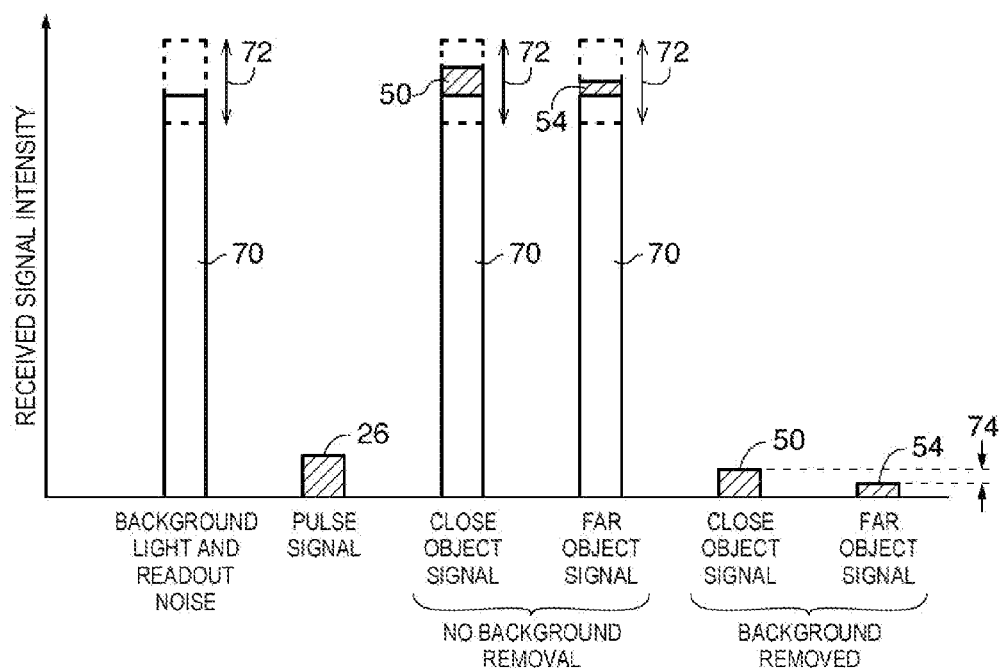
FIG. 5 is an illustrative graph showing how removal of background light using an electronic device of the type shown in FIG. 1 may help determine depth information in accordance with an embodiment of the present invention.

In this way, emitter 20 and time-of-flight image pixels such as pixels 32 may be used to gather depth information about the scene from relative brightness or detected, reflected light. However, as shown in FIG. 5, it may be beneficial to remove background light signals from detected signals before constructing a depth image. In the example of FIG. 5, an image pixel such as a time-of-flight image pixel 32 may be configured to detect a background signal such as signal 70 in the absence of an emitted light pulse that includes only background light and associated noise such as photon noise, read noise or other noise. Due to the noise signal associated with background signal 70, background signal 70 may be uncertain by an amount 72. A light emitter such as emitter 20 may emit a light pulse 26 having a signal intensity that is smaller than the intensity of background signal 70.

After emission of light pulse 26, time-of-flight image pixels such as pixels 32 of FIG. 2 may detect reflected return pulses such as pulses 50 and 54 in addition to background signal 70 that is uncertain by an amount 72. Because background signal 70 may be larger than pulse 26, return pulses 50 and 54 may be smaller than the amount 72 of noise associated with signal 70. For this reason, time-of-flight image pixels such as pixels 32 may be configured to remove background signal 70 from detected image light signals. Time-of-flight image pixels such as pixels 32 may be configured to sample background signal 70 and to readout only signal from subsequent integrations that is in excess to background signal 70. Time-of-flight image pixels such as pixels 32 may therefore be configured to provide close object signal 50 and far object signal 54 with background signal 70 removed so that a relative difference 74 may be detected between signals such as signals 50 and 54.

Figure 6:
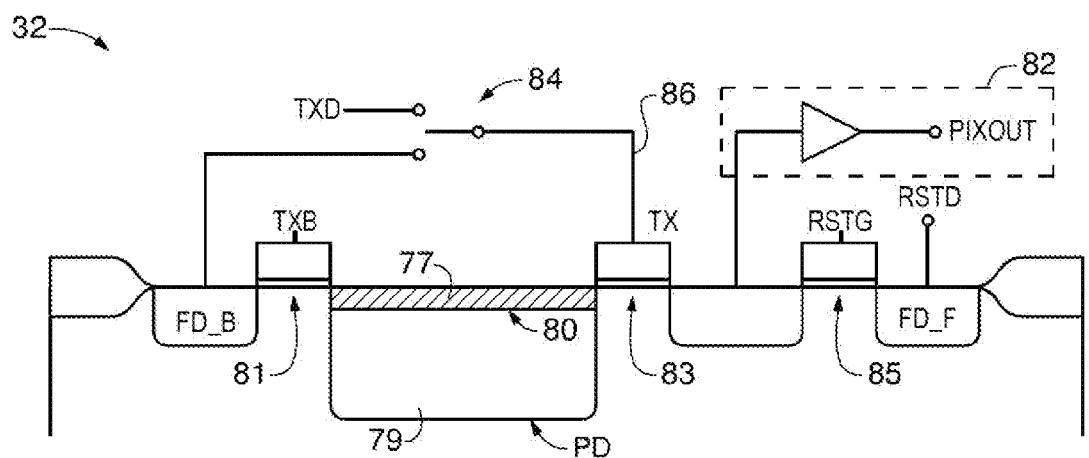
FIG. 6 is a schematic diagram of an illustrative time-of-flight image sensor pixel in accordance with an embodiment of the present invention.

FIG. 6 is a schematic diagram of an illustrative time-of-flight image pixel 32. As shown in FIG. 6, time-of-flight image pixel 32 may include a photosensitive element such as photodiode PD and charge storage regions such floating diffusion regions FD_B and FD_F. Charge storage regions FD_B and FD_F may be implemented using a region of doped semiconductor (e.g., a doped silicon region formed in a silicon substrate by ion implantation, impurity diffusion, or other doping techniques). The doped semiconductor region (i.e., the floating diffusion FD) exhibits a capacitance that can be used to store the charge that has been transferred from photodiode PD. The signal associated with the stored charge on node FD_F may be conveyed processing circuitry such as processing circuitry 18 of FIG. 1 using readout circuitry 82.

Photodiode PD may be implemented using a p-n junction formed from an interface such as interface 80 between doped semiconductor regions 77 and 79 (i.e., an interface between a p-type semiconductor and an n-type semiconductor) for converting captured light into electrical charge. Region 77 may be implemented using a region of p-type doped semiconductor and region 79 may be implemented using an n-type doped semiconductor. However, this is merely illustrative. If desired, region 77 may be implemented using a region of n-type doped semiconductor and region 79 may be implemented using a p-type doped semiconductor.

Time-of-flight pixel 32 may include reset transistors such as reset transistor 85 that receive a reset signal RSTG. Reset transistor 85 may include a source/drain terminal coupled to a reset voltage RSTD. Reset voltage RSTD may be, for example, a positive power supply voltage (sometimes denoted as Vaa), a ground voltage (sometimes denoted as AGND), etc. Time-of-flight pixel 32 may include transfer transistors (transfer gates) such as transfer transistor 81 that receives a transfer signal TXB for transferring electric charge from photodiode PD to charge storage region FD_B and transfer transistor 83 that receives a transfer signal TX for transferring electric charge from photodiode PD to charge storage region FD_F.

As shown in FIG. 6, transfer transistor 83 may have a gate terminal such as terminal 86 that is coupled to charge storage region FD_B. Time-of-flight image pixel 32 may include a switch such as switch 84 that allows gate 86 of transfer transistor 83 to be connected to charge storage region FD_B so that transfer signal TX may be equal to the voltage on charge storage region FD_B. Switch 84 may allow gate 86 to alternatively be connected to an additional transfer voltage so that transfer transistor 83 may receive a different transfer control signal such as transfer control signal TDX (e.g., a positive power supply voltage Vaa, a ground voltage AGND, etc.).

Signals associated with the charge converted by a photodiode or current generated by time-of-flight pixel 32 (sometimes referred to herein as depth-image data) may be conveyed to processing circuitry 18 of electronic device 10 (see FIG. 1) through readout circuitry such as circuitry 82 that includes components such as row select transistors, source-follower transistors, or other components associated with time-of-flight pixel 32. Some components of time-of-flight pixel 32 (e.g., row select transistors, charge storage regions, reset transistors, etc.) may be shared among multiple time-of-flight pixels. Image data that has been captured by time-of-flight pixels 32 may be processed and stored using processing circuitry 18. Processed image data may, if desired, be provided to external equipment (e.g., a computer or other device) using wired and/or wireless communications paths coupled to processing circuitry 18.

Figure 7:
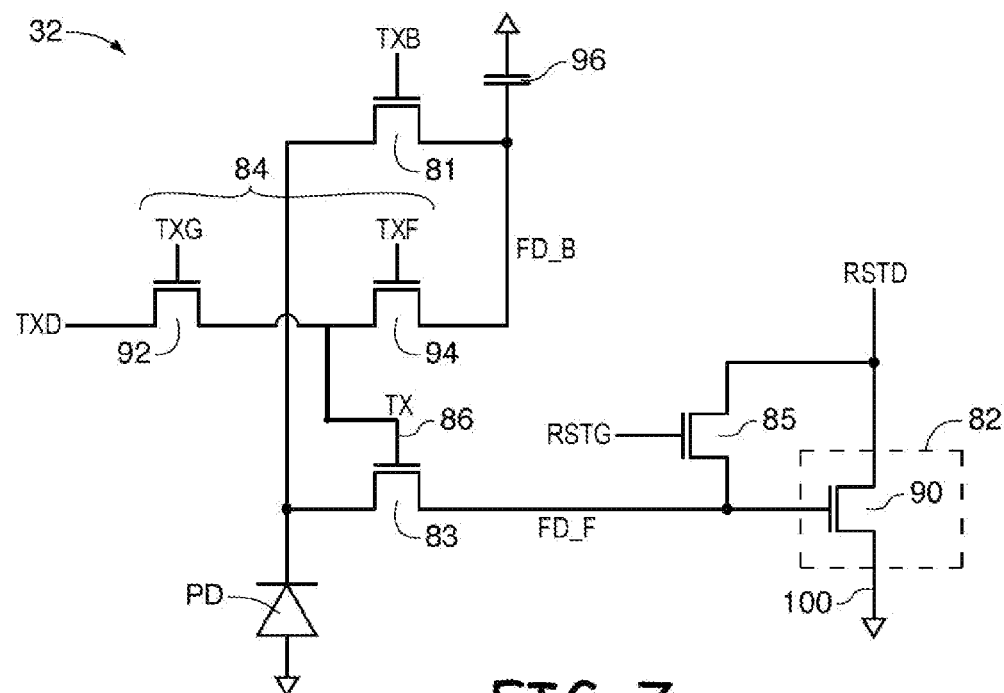
FIG. 7 is a diagram of an illustrative time-of-flight image sensor pixel in accordance with an embodiment of the present invention.
Figure 8:
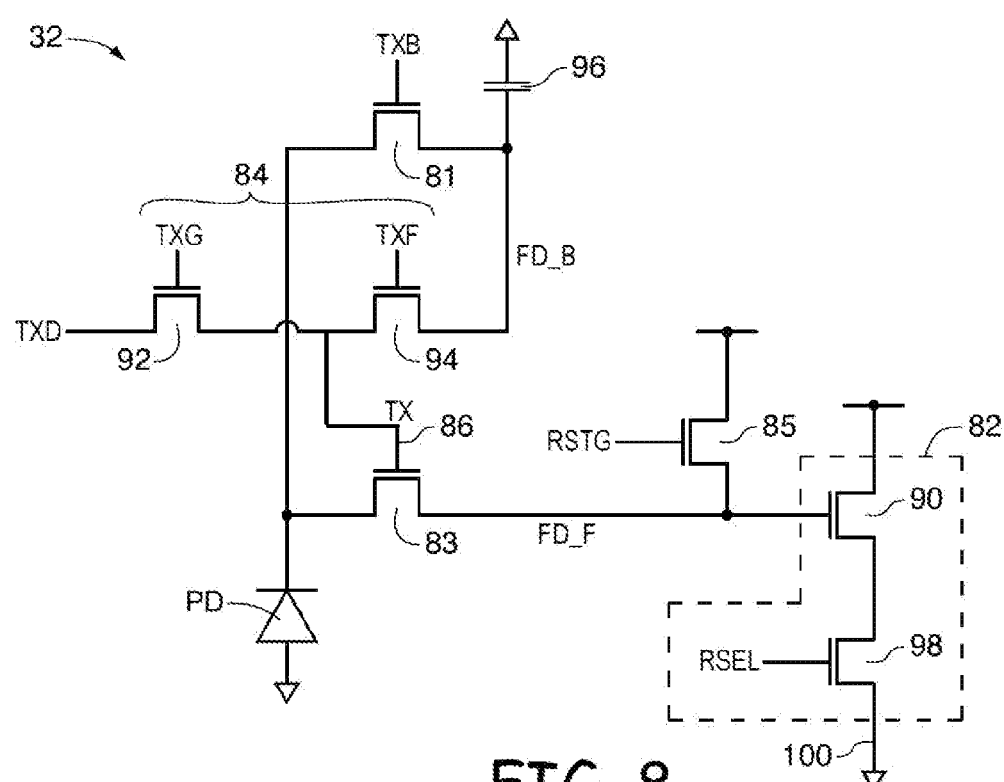
FIG. 8 is a diagram of an illustrative time-of-flight image sensor pixel in accordance with an embodiment of the present invention.
Figure 9:
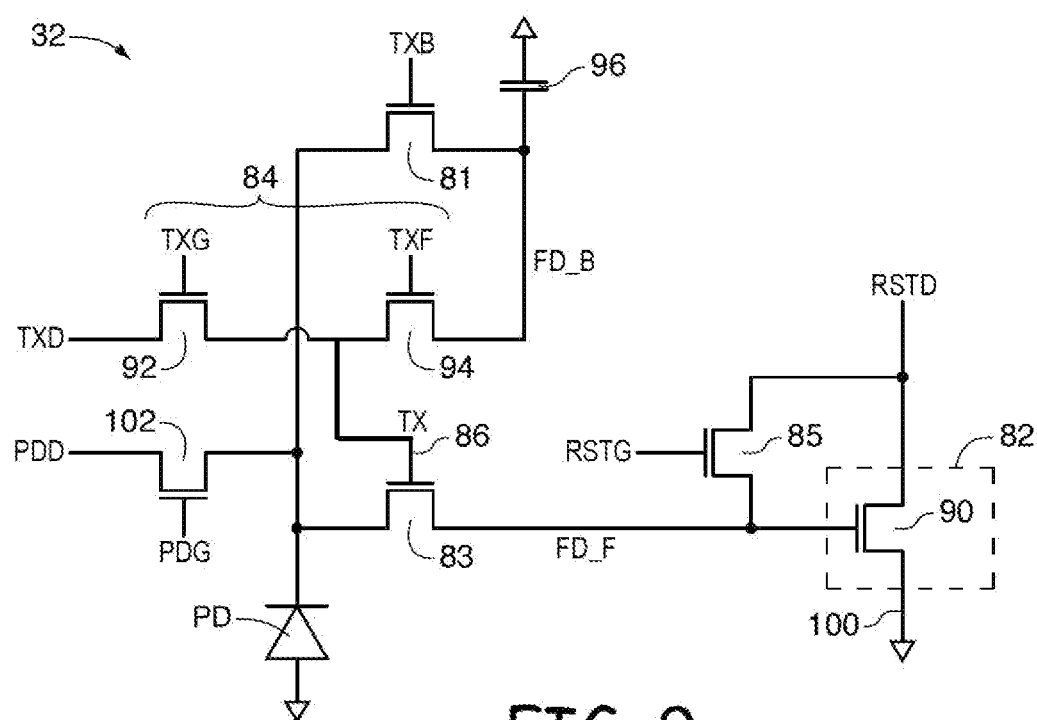
FIG. 9 is a diagram of an illustrative time-of-flight image sensor pixel in accordance with an embodiment of the present invention.

Various illustrative embodiments of time-of-flight image pixel 32 having a transfer transistor having a gate that is coupled to a charge storage region are shown in FIGS. 7, 8, and 9. As shown in FIG. 7, photodiode PD may be coupled to multiple charge storage regions such as floating diffusion regions FD_B and FD_F. Photodiode PD may be coupled to floating diffusion region FD_F via transfer transistor 83 and to floating diffusion region FD_B via transfer transistor 81. Gate 86 of transfer transistor 83 may be coupled to a source/drain terminal of transfer transistor 92 and a source/drain terminal of transfer transistor 94. In combination, transistors 92 and 94 may form switch 84 for selectively connecting gate 86 to floating diffusion region FD_B (e.g., by asserting transfer signal TXF and de-asserting transfer signal TXG) or to another transfer control signal such as signal TXD (e.g., by de-asserting transfer signal TXF and asserting transfer signal TXG).

As shown in FIG. 7, if desired, floating diffusion region FD_B may include an additional capacitor such as capacitor 96 for increasing the well depth of floating diffusion region FD_B (i.e., the amount of charge that can be stored). During exposure, light may be converted into electric charge by photodiode PD. Charges accumulated by photodiode PD may be transferred to floating diffusion region FD_B by activating transfer transistor 81 or to floating diffusion region FD_F by activating transfer transistor 83. The quantity of charge transferred from photodiode PD to floating diffusion region FD_B may be determined by the voltage TX applied to gate 86 of transfer transistor 83 (e.g., whether gate 86 is coupled to floating diffusion region FD_B or to another voltage source).

As shown in FIG. 7, pixel 32 may be coupled to a readout circuit such as readout circuit 82. Readout circuit 82 may include a source follower transistor such as transistor 90 having a gate terminal coupled to floating diffusion region FD_F for converting charge stored on floating diffusion region FD_F into a voltage to be readout along path 100 (e.g., to processing circuitry 18 of FIG. 1). Readout circuit 82 may include reset transistor 85. In the example of FIG. 7, reset transistor 85 includes a first source/drain terminal connected to floating diffusion region FD_F and a second source/drain terminal connected to a reset voltage RSTD. Source follower transistor 90 may include a gate terminal connected to a first source/drain terminal of reset transistor 85 and a source/drain terminal that is connected to a second source/drain terminal of reset transistor 85. However, this is merely illustrative.

If desired, source/drain terminals of source follower transistor 90 may be free of connections to source/drain terminals of reset transistor 85 as shown in FIG. 8. In the example of FIG. 8, source follower transistor 90 may include a gate terminal connected to a source/drain terminal of reset transistor 85 and a source/drain terminal that is connected to a row select transistor such as row select transistor 98. Row select transistor 98 may include a gate terminal that receives a row select signal RSEL that selects a row of pixels including pixel 32. When row select signal RSEL is asserted, charge stored on floating diffusion region FD_F may be converted to a voltage signal by source follower transistor 90 and the pixel signal may be read out along path 100.

It may be desirable to be able to reset photodiode PD without resetting floating diffusion region FD_F. As shown in FIG. 9, time-of-flight pixel 32 may therefore be provided with an additional reset transistor such as transistor 102 having a source/drain terminal coupled to photodiode PD and a second source/drain terminal coupled to a reset voltage PDD. Transistor 102 may receive a control signal PDG for resetting photodiode PD. Photodiode PD may be reset between subsequent light collection periods during which return pulses such as pulses 50, 52, and 54 of FIG. 5 are incident on photodiode PD.

Some of the charges generated by photodiode PD during exposure periods during which return pulses such as pulses 50, 52, and 54 are incident on photodiode PD may be transferred to floating diffusion region FD_F after each exposure period. Photodiode PD may then be reset using transistor 102 without resetting floating diffusion region FD_F so that additional charges may be collected due to additional return pulses. The additional charges may then be transferred to floating diffusion region FD_F where the original charges are still stored. In this way, multiple integrations of charges generated by light pulses reflected by objects after emission (e.g. by emitter 20 of FIG. 1) may be accumulated on floating diffusion region FD_F prior to readout of pixel 32.

During transfer of charges to floating diffusion region FD_F, gate 86 of transistor 83 may be coupled to floating diffusion region FD_B. Floating diffusion region FD_B may store charges transferred from photodiode PD following a previous exposure period in which no pulse was emitted by emitter 20. Photodiode PD may be reset between transfer of charges to floating diffusion region FD_B and accumulation of charges due to return pulses such as pulses 50, 52, and 54 incident on photodiode PD.

Figure 10:
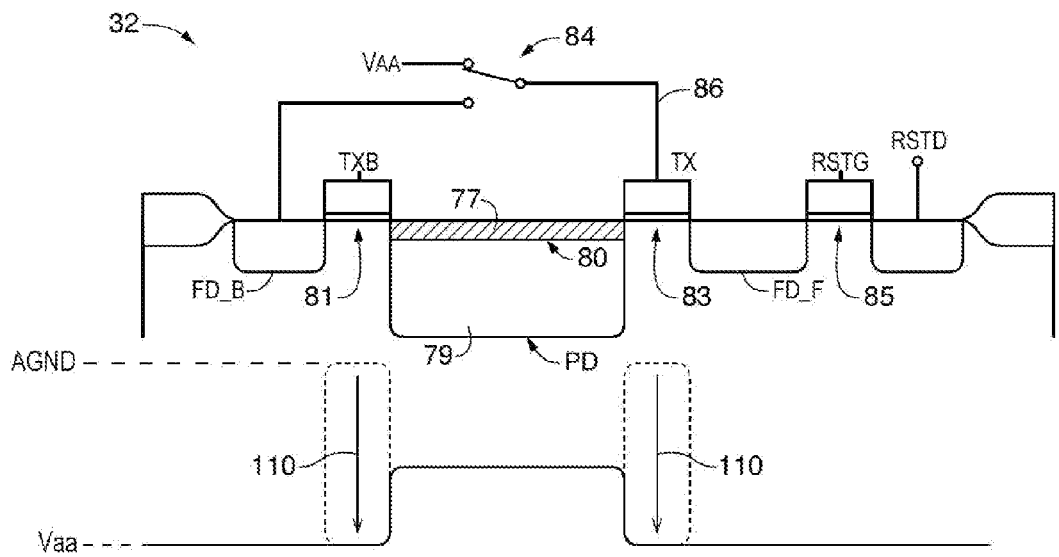
FIG. 10 is a schematic diagram of an illustrative time-of-flight image sensor pixel showing how the pixel may be reset in accordance with an embodiment of the present invention.

FIGS. 10, 11, 12, 13, 14, 15, 16, and 17 show illustrative charge storage configurations of time-of-flight image pixel 32 during operation electronic device 10. As shown in FIG. 10, before image data is acquired (e.g., before exposure of photodiode PD to light for conversion of light into electric charge), reset control signal RSTG, and transfer signals TXB and TX may be asserted to reset pixel 32. This turns on reset transistor 85 and transfer transistors 81 and 83 to reset charge storage nodes FD_B and FD_F (also referred to as floating diffusion regions) to a power supply voltage Vaa as indicated by arrows 110. The reset control signal RSTG may then be deasserted to turn off reset transistor 85.

Figure 11:
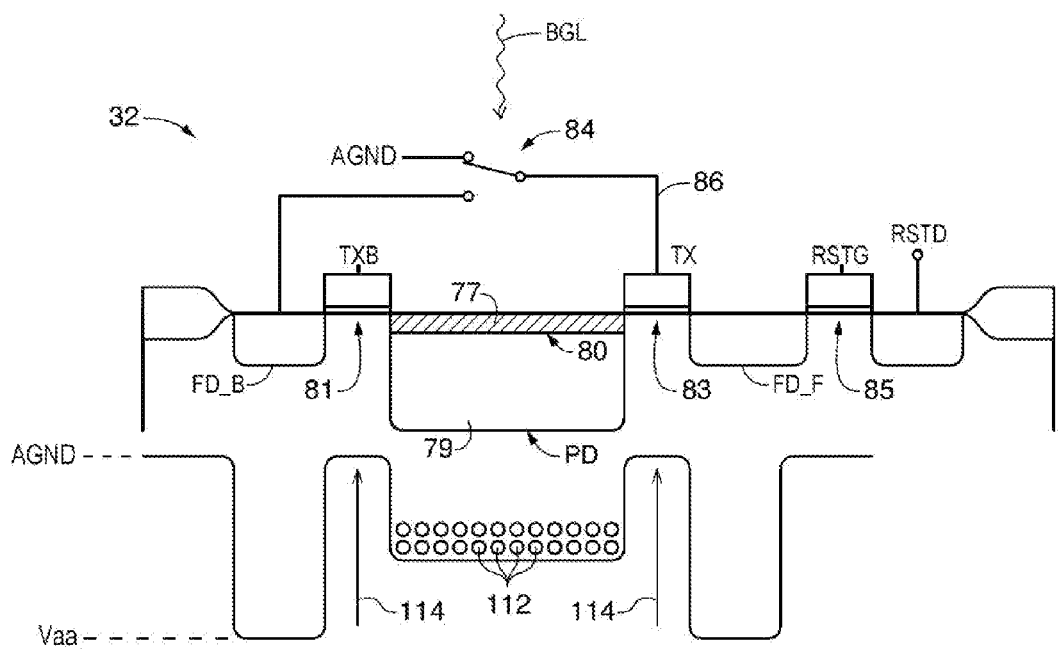
FIG. 11 is a schematic diagram of an illustrative time-of-flight image sensor pixel showing how charges may be collected during exposure to background light from a real-world scene in accordance with an embodiment of the present invention.

After the reset process is complete, as shown in FIG. 11, transfer gate control signals TX and TXB may be deasserted (e.g., transfer gates associated with transistors 81 and 83 may be coupled to a ground voltage AGND) as indicated by arrows 114. With transfer control signals TX and TXB deasserted, photodiode PD may be exposed to background light BGL for a predetermined amount of time (e.g., the exposure time). Background light BGL may include light from a real-world scene in the absence of an emitted light pulse from electronic device 10 (e.g., a pulse of infrared light from emitter 20 of FIG. 1). Photodiode PD may convert background light BGL into electric charges 112.

Figure 12:
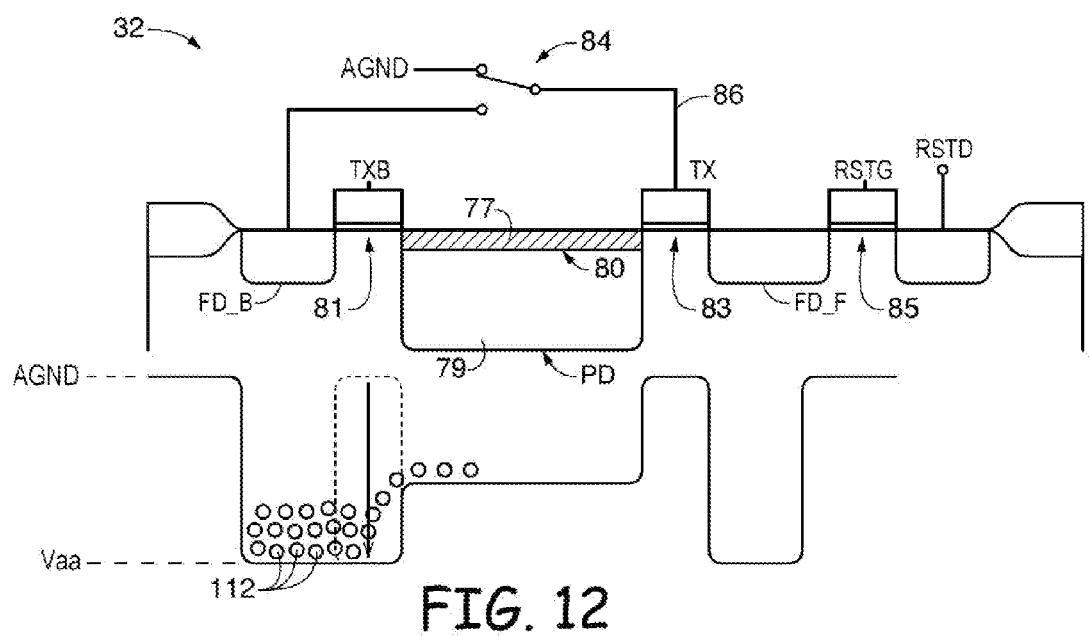
FIG. 12 is a schematic diagram of an illustrative time-of-flight image sensor pixel showing how collected charges associated with background light may be transferred to a charge storage region in accordance with an embodiment of the present invention.

As shown in FIG. 12, charges 112 may be transferred from photodiode PD to charge storage region FD_B. Charges 112 may be transferred to region FD_B by asserting transfer signal TXB (e.g., coupling a gate terminal of transistor 81 to supply voltage Vaa) thereby activating transistor 81.

Figure 13:
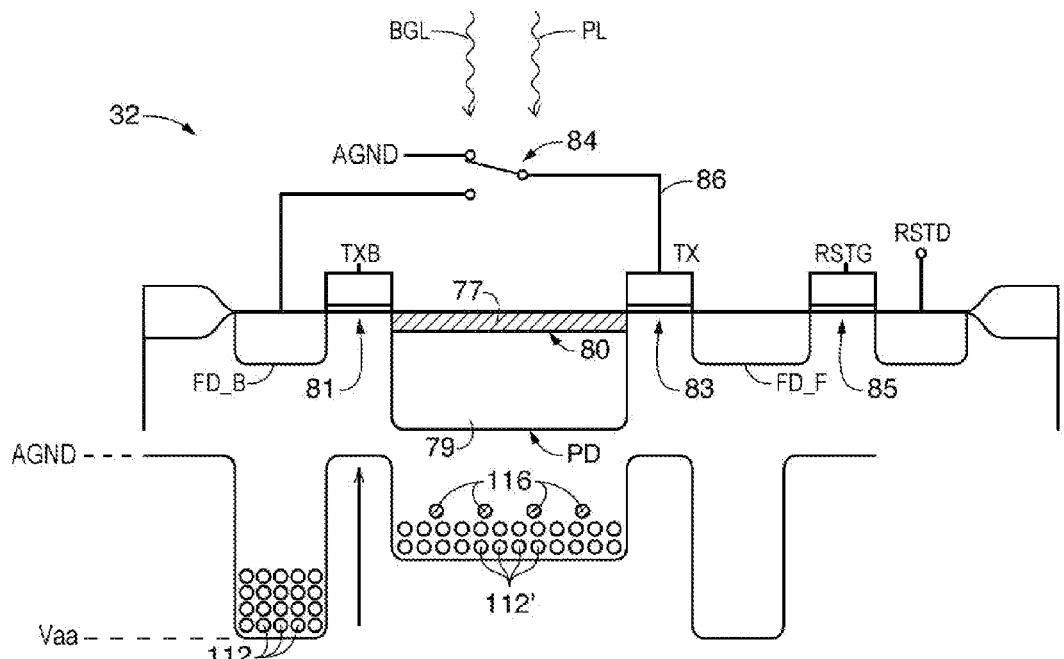
FIG. 13 is a schematic diagram of an illustrative time-of-flight image sensor pixel showing how additional charges may be collected in response to a reflected portion of a light pulse during exposure to a real-world scene in accordance with an embodiment of the present invention.

Following transfer of charges 112 to storage region FD_B, a light emitter associated with device 10 (e.g., emitter 20 of FIG. 1) may emit a pulse of light that is reflected from objects in a scene onto photodiode PD. As shown in FIG. 13, reflected pulse light PL and background light BG may be incident on photodiode PD. Photodiode PD may convert pulse light PL and background light BG into electric charges 116 and 112' respectively while collecting light for the same predetermined exposure time used in collecting background light BGL as described in connection with FIG. 11. Because electric charges are indistinguishable from other electric charges, time-of-flight image pixel 32 may be configured to separate electric charges 112' and 116 using a previous measurement of the amount of charge produced by photodiode PD in response to background light BGL during the same exposure time (i.e., charges 112 stored on floating diffusion region FD_B).

Figure 14:
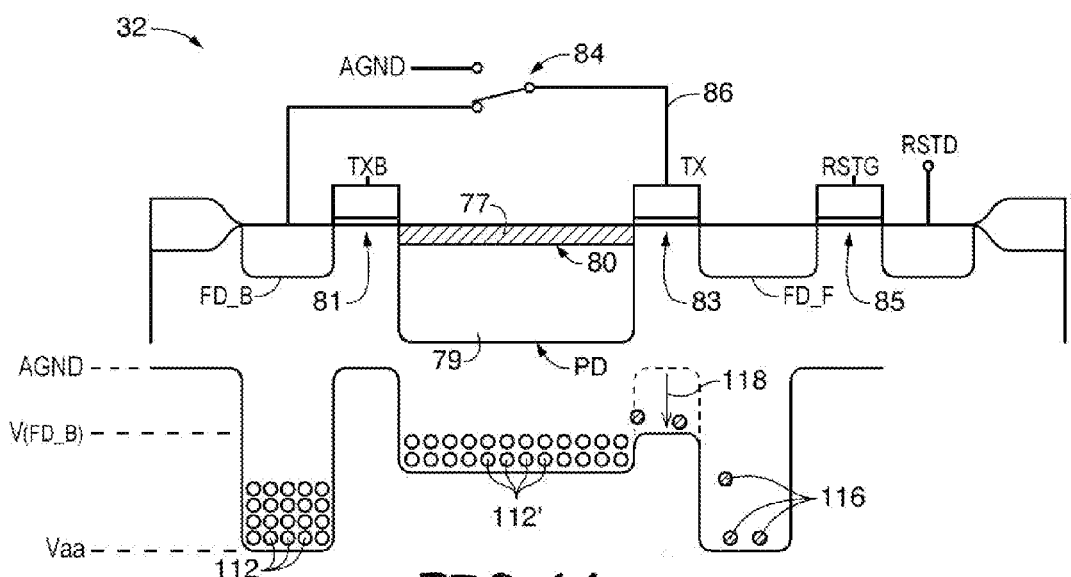
FIG. 14 is a schematic diagram of an illustrative time-of-flight image sensor pixel showing how collected charges associated with a light pulse may be transferred to a charge storage region in accordance with an embodiment of the present invention.

As shown in FIG. 14, time-of-flight image pixel 32 may be configured to separate electric charges 112' and 116 by coupling gate 86 of transfer transistor 83 to charge storage region FD_B where charges 112 are stored. Coupling gate 86 of transistor 83 charge storage region FD_B where charges 112 may couple gate 86 to a voltage V(FD_B) determined by the amount of charges 112 stored on region FD_B. As shown in FIG. 14, this may allow charges 116 in excess of the amount of charges 112 stored on region FD_B to be transferred to floating diffusion region FD_F. Following transfer of charges 116 to charge storage region FD_F, charges 112' may remain on photodiode PD. Charges 112' and charges 112 may be a substantially equal amount of charge. Gate 86 may be coupled to charge storage region FD_B by activating transistor 94 (see FIGS. 7, 8, and 9) by asserting transfer signal TXF). Activating transistor 94 may partially activate transistor 83 as indicated by arrow 118 of FIG. 14 to transfer charges 116 to storage region FD_F.

Figure 15:
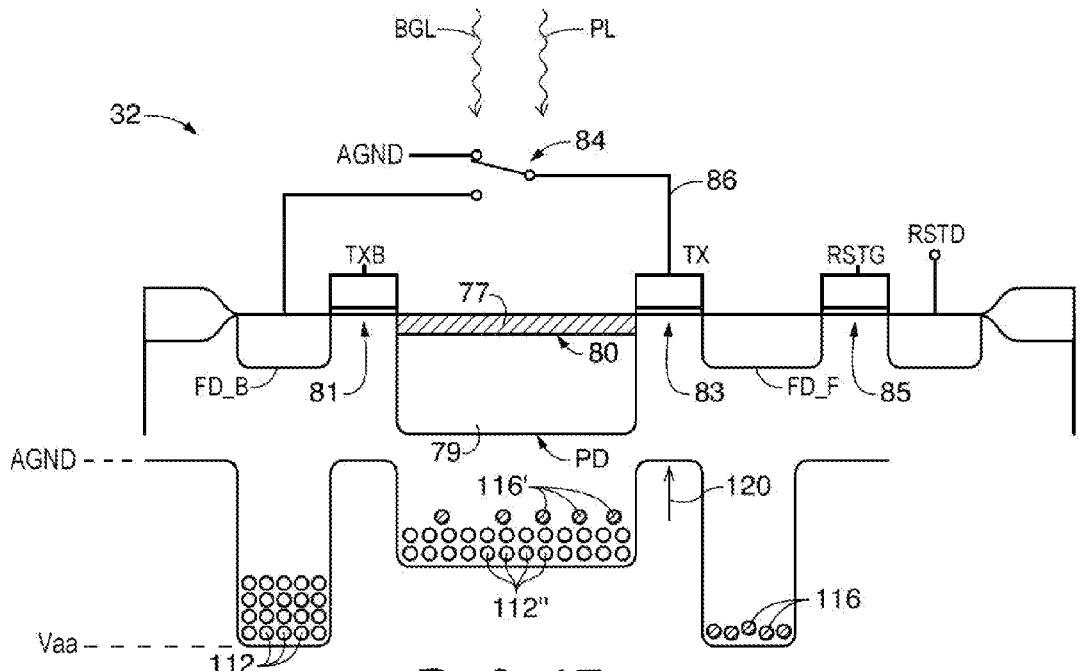
FIG. 15 is a schematic diagram of an illustrative time-of-flight image sensor pixel showing how a second exposure to a real-world scene and a light pulse may generate charges in accordance with an embodiment of the present invention.
Figure 16:
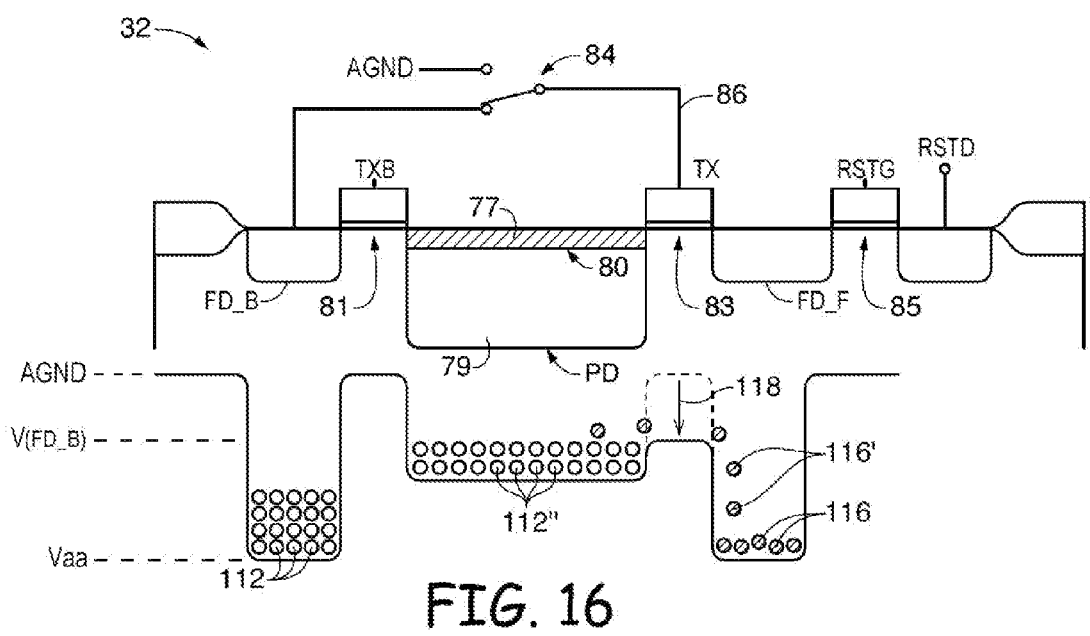
FIG. 16 is a schematic diagram of an illustrative time-of-flight image sensor pixel showing how collected charges associated a second exposure with a light pulse may be transferred to a charge storage region in accordance with an embodiment of the present invention.
Figure 17:
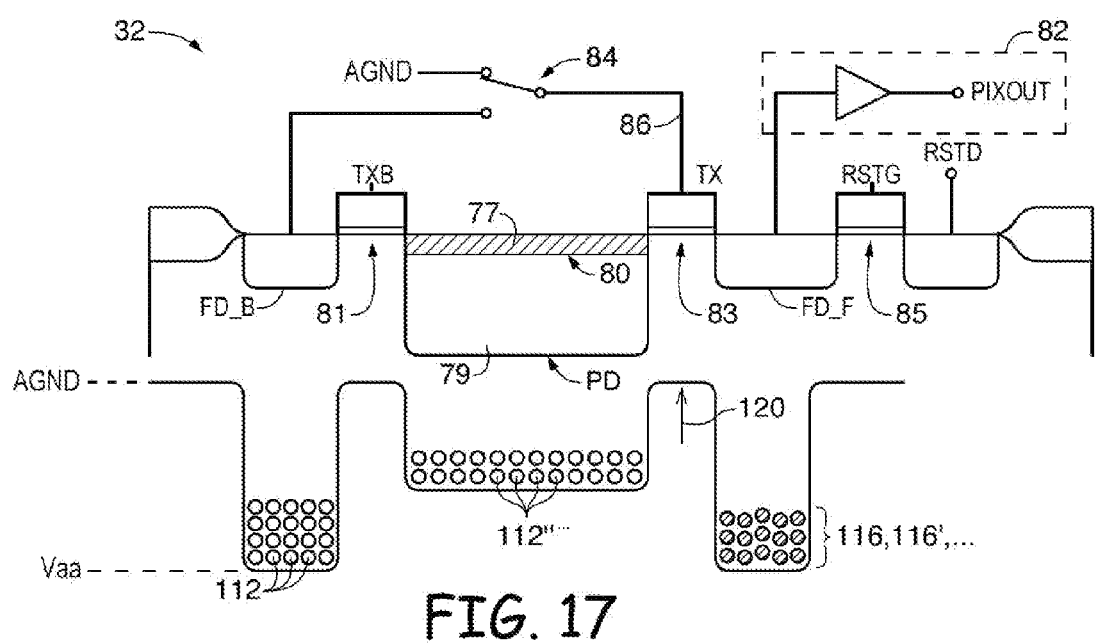
FIG. 17 is a schematic diagram of an illustrative time-of-flight image sensor pixel showing how collected charges associated background light may be stored on a first charge storage region and collected charges associated with multiple light pulses may be stored on a second charge storage region in accordance with an embodiment of the present invention.

As shown in FIGS. 15, 16, and 17, the steps described above in connection with FIGS. 11, 12, 13, and 14 may be repeated following a reset of photodiode PD (i.e., a removal of charges 112' stored on photodiode PD). Photodiode PD may be reset, for example, by activating transistor 102 of FIG. 9. Resetting photodiode PD by activating transistor 102 may allow additional charges generated from pulse light PL to be stored with charges 116 on storage region FD_F. However, this is merely illustrative. If desired, a time-of-flight signal based on charges 116 on storage region FD_F may be read out using a readout circuit such as circuit 82 of FIG. 6 and photodiode PD and storage region FD_F may both be reset before repeating the steps described above in connection with FIGS. 11, 12, 13, and 14.

In configurations in which photodiode PD is reset without resetting floating diffusion region FD_F, photodiode PD may be subsequently exposed to background light BGL and pulse light PL from a subsequent pulse by emitter 20 while gate 86 is coupled to ground voltage AGND as shown in FIG. 15. Background light BGL and subsequent pulse light PL may be converted into electric charges 112" and 116' respectively.

As shown in FIG. 16, gate 86 of transistor 83 may be subsequently coupled to charge storage region FD_B in order to transfer charges 116' to charge storage region FD_F. Following transfer of charges 116' to charge storage region FD_F, charges 112" may remain on photodiode PD. Charges 112" and charges 112 may be a substantially equal amount of charge. Following transfer of charges 116' to charge storage region FD_F, charge storage region FD_F may include both charges 116' and 116 from subsequent pulses of emitter 20.

As shown in FIG. 17, the steps described above in connection with FIGS. 15 and 16 may be repeated any number of times. Following transfer of charges 116, 116' and charges associated with further pulses of light by emitter 20 to floating diffusion region FD_F, charges such as charges 112" . . . may remain on photodiode PD until a subsequent reset of photodiode PD or pixel 32. Charges 116, 116', . . . may be transferred to control circuitry such as storage and processing circuitry 18 of FIG. 1 for using a source follower transistor to convert charges 116, 116', . . . into a time-of-flight signal associated with an object in the field-of-view of time-of-flight pixel 32. Circuitry 18 may be used to combine time-of-flight signals from multiple pixels 32 (e.g., in an array of time-of-flight image pixels, multiple arrays of time-of-flight pixels, etc.) to form a depth image in which the value of each pixel in the depth image contains information relating to the distance to an object in that pixel.

Figure 18:
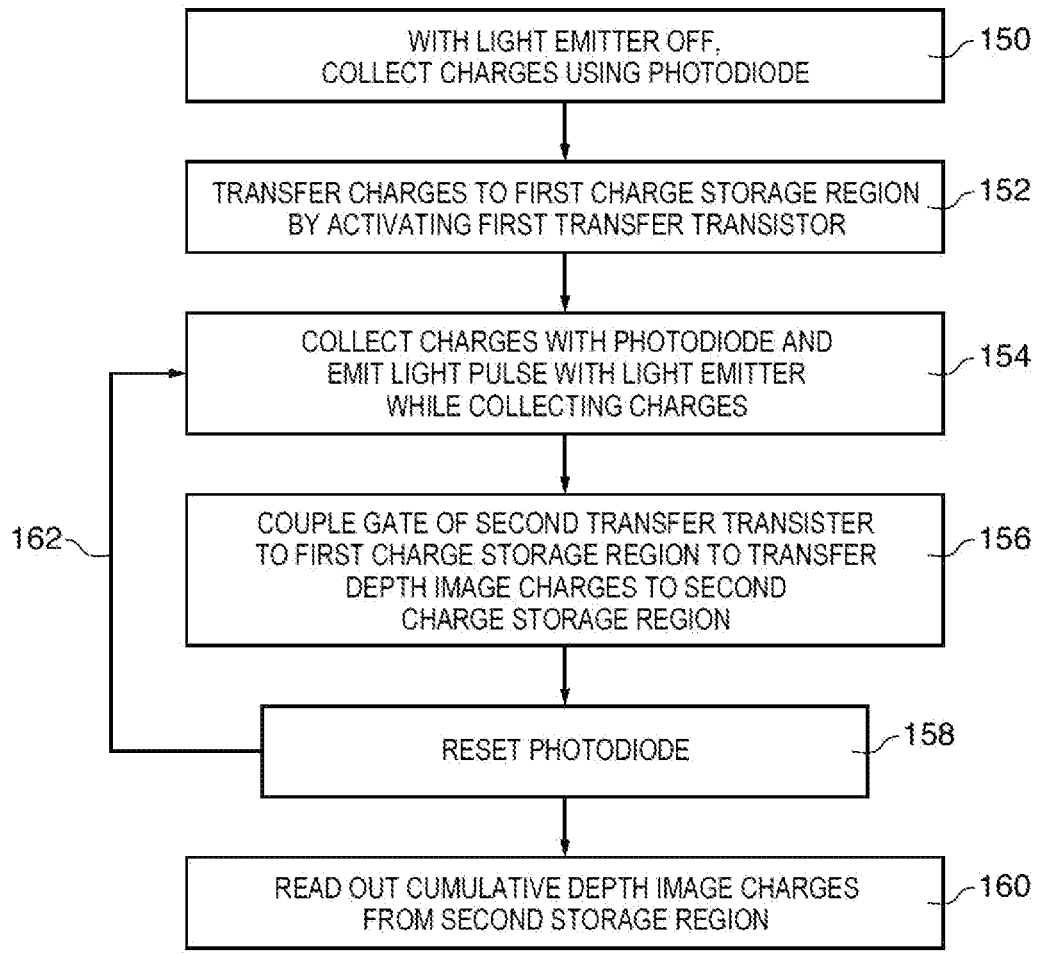
FIG. 18 is a flow chart of illustrative steps involved in using an electronic device having time-of-flight image sensor pixels in accordance with an embodiment of the present invention.

FIG. 18 is a flow chart of illustrative steps that may be used in acquiring depth images using an electronic device having time-of-flight image pixels and a light pulse emitter.

At step 150, with the light pulse emitter off, charges may be collected using a photodiode such as photodiode PD associated with time-of-flight image pixels such as time-of-flight image pixel 32 in response to background light such as background light BGL for a predetermined exposure time.

At step 152, charges collected using photodiode PD may be transferred to a charge storage region such as floating diffusion region FD_B by activating a transfer transistor coupled between the photodiode and the charge storage region.

At step 154, charges may be again collected using photodiode PD for the same predetermined exposure time. During the predetermined exposure time, a pulse of, for example, infrared light may be emitted by a non-visible light emitter such as non-visible light emitter 20 of FIG. 1. Charges collected by photodiode PD may be generated by photodiode PD in response to background light BGL and pulsed light from emitter 20 that has been reflected from objects in the field-of-view of time-of-flight image pixel 32.

At step 156, a second transfer transistor such as transfer transistor 83 coupled between photodiode PD and a second charge storage region such as floating diffusion region FD_F may be partially activated by coupling a gate such as gate terminal 86 of transistor 83 to floating diffusion region FD_B. Coupling gate terminal 86 to floating diffusion region FD_B may allow charges generated by photodiode PD in response to pulse light PL (sometimes called depth-image charges) to be transferred to charge storage region FD_F.

At step 158, photodiode PD may be reset. If desired, charge storage regions FD_F and FD_B may also be reset. In configurations in which charge storage region FD_F is also reset, a voltage associated with charges stored on charge storage region FD_F may be read out to circuitry such as storage and processing circuitry 18 of FIG. 1 prior to resetting charge storage region FD_F. In configurations in which charge storage region FD_B is reset, steps 150, 152, 154 and 156 may be repeated for subsequent collection of depth-image charges.

As indicated by arrow 162, if desired, following reset of photodiode PD, steps, 154, and 156 may be repeated to collect subsequent measurements of depth-image information by collecting charges associated with subsequent pulses of light by emitter 20. Repeating steps 154 and 156 may allow collection of a stronger depth-image signal without increasing the intensity of emitted light pulses from emitter 20.

At step 160, cumulative depth-image charges (i.e., all charges stored on floating diffusion region FD_F following multiple pulses of light from emitter 20) may be read out from charge storage region FD_F to circuitry such as storage and processing circuitry 18.

Circuitry 18 may be used to combine time-of-flight signals (depth-image signals) from multiple pixels 32 (e.g., in an array of time-of-flight image pixels, multiple arrays of time-of-flight pixels, etc.) to form a depth image in which the value of each pixel in the depth image contains information relating to the distance to an object in that pixel.

Various embodiments have been described illustrating electronic devices that include time-of-flight image pixels configured to measure the time of flight of an emitted light pulse for sensing distance information about objects in a scene. Emitted light pulses may be generated by a light pulse emitter on the electronic device and reflected from objects in the field-of-view of the time-of-flight image pixels. Time-of-flight image pixels may be configured to measure differences in time-of-flight between reflected portions of emitted light pulses using differences in brightness of the reflected portions. Time-of-flight image sensors may be configured to remove background light contamination of reflected portions of emitted light pulses.

A time-of-flight image pixel may include a photosensitive element such as a photodiode, and first and second charge storage regions coupled to the photosensitive element. A time-of-flight image pixel may include a first transfer transistor coupled between the photosensitive element and the first charge storage region and a second transfer transistor coupled between the photosensitive element and the second charge storage region. The second transfer transistor may include a gate terminal that is coupled to the first charge storage region.

A time-of-flight image pixel may include a third transfer transistor having first and second source/drain terminals. The first source/drain terminal of the third transfer transistor may be connected to the gate terminal of the second transfer transistor and the second source/drain terminal of the third transfer transistor may be connected to the first charge storage region.

A time-of-flight image pixel may include a fourth transfer transistor having a first source/drain terminal that is coupled to the gate terminal of the second transfer transistor and a reset transistor having a first source/drain terminal that is coupled to the second charge storage region and a second source/drain terminal coupled to a source/drain terminal of a source follower transistor having a gate terminal connected to the second charge storage region. If desired, a time-of-flight image pixel may include an additional reset transistor having a first source/drain terminal that is coupled to the photosensitive element.

If desired, the time-of-flight image pixel may include a reset transistor having a first source/drain terminal that is coupled to the second charge storage region, a source follower transistor having a gate terminal connected to the second charge storage region, and a row select transistor coupled to the source follower transistor.

The electronic device may further include a light pulse emission component such as a non-visible light pulse emitter configured to emit pulses of non-visible light. The electronic device may include an array of image sensors. The array of image sensors may include a red image sensor, a blue image sensor, a green image sensor or other image sensors. Each of the image sensors in the array of image sensors may include an array of time-of-flight image pixels. Time-of-flight image pixels may be configured to collect background light and reflected portions of the emitted pulses of non-visible light and to store charges generated by the background light on the first charge storage region and to store charges generated by the reflected portions of the emitted pulses of non-visible light on the second charge storage region.

The electronic device may include processing circuitry configured to extract depth information from a depth-image signal generated by the time-of-flight image pixels. The processing circuitry may be configured to combine image data from the red image sensor, the blue image sensor, and the green image sensor to form a color image.

During operation of the electronic device, time-of-flight image pixels may be configured to convert background light into electric charges and to transfer the electric charges from the photosensitive element to the first charge storage region. A light pulse emitter may be configured to emit a pulse of non-visible light. Time-of-flight image pixels may be configured to convert additional background light and a reflected portion of the emitted pulse of non-visible light into additional electric charges and to transfer a portion of the additional electric charges (e.g., the portion corresponding to the reflected portion of the emitted pulse of non-visible light) to the second charge storage region. Transferring the portion of the additional electric charges may include connecting the gate terminal of the second transfer transistor to the first charge storage region on which the electric charges are stored by activating the fourth transfer transistor.

During operation, the photosensitive element may be reset to remove a remaining portion of the additional electric charges from the photosensitive element before a subsequent pulse of non-visible light may be emitted from the light pulse emitter. Time-of-flight image pixels may be configured to convert further additional background light and a reflected portion of the subsequent emitted pulse of non-visible light into further additional electric charges and to transfer a portion of the further additional electric charges (e.g., the portion corresponding to the reflected portion of the subsequent emitted pulse of non-visible light) to the second charge storage region on which the portion of the additional electric charges is stored.

Time-of-flight image pixels may be configured to convert the portion of the additional electric charges and the portion of the further additional electric charges into a depth-image signal. Processing circuitry may be used to extract distance information from the depth-image signal and to process the distance information to form a portion of a depth image that includes depth-image pixel values that correspond to the distance of an object to the electronic device.

The foregoing is merely illustrative of the principles of this invention which can be practiced in other embodiments.

What is claimed is:

1. A time-of-flight image pixel comprising:
   a photosensitive element;
   first and second charge storage regions coupled to the photosensitive element;
   a first transfer transistor coupled between the photosensitive element and the first charge storage region; and
   a second transfer transistor coupled between the photosensitive element and the second charge storage region, wherein the second transfer transistor includes a gate terminal that is coupled to the first charge storage region.

2. The time-of-flight image pixel defined in claim 1, further comprising:
   a third transfer transistor having a first source-drain terminal and a second source-drain terminal, wherein the first source-drain terminal of the third transfer transistor is connected to the gate terminal and wherein the second source-drain terminal of the third transfer transistor is connected to the first charge storage region.

3. The time-of-flight image pixel defined in claim 2, further comprising:
   a fourth transfer transistor having a first source-drain terminal that is coupled to the gate terminal.

4. The time-of-flight image pixel defined in claim 2, further comprising:
   a reset transistor having a first source-drain terminal and a second source-drain terminal, wherein the first of the reset transistor is coupled to the second charge storage region; and
   a source follower transistor having a gate terminal connected to the second charge storage region and a source-drain terminal that is coupled to the second source-drain terminal of the reset transistor.

5. The time-of-flight image pixel defined in claim 4, further comprising:
   an additional reset transistor having a source-drain terminal that is coupled to the photosensitive element.

6. The time-of-flight image pixel defined in claim 2, further comprising:
   a reset transistor having a first source-drain terminal that is coupled to the second charge storage region;
   a source follower transistor having a gate terminal connected to the second charge storage region; and
   a row select transistor coupled to the source follower transistor.

7. The time-of-flight image pixel defined in claim 1, further comprising:
   control circuitry configured to control the first transfer transistor to couple the first charge storage region to the photosensitive element during a background light capture period.

8. The time-of-flight image pixel defined in claim 7, further comprising:
   control circuitry configured to control the second transfer transistor to couple the second charge storage region to the photosensitive element during a non-visible light capture period.

9. An electronic device, comprising:
   control circuitry;
   a light pulse emission component configured to emit pulses of non-visible light; and
   an array of time-of-flight image pixels, wherein each time-of-flight image pixel comprises:
      a photodiode;
      a first charge storage region;
      a first transfer transistor that is coupled between the photodiode and the first charge storage region, wherein the control circuitry is configured to control the first transfer transistor to transfer charges from the photodiode to the first charge storage region after a background light collecting period of the electronic device;
      a second charge storage region;
      a second transfer transistor that is coupled between the photodiode and the second charge storage region; and
      a switch configured to selectively connect a gate terminal of the second transfer transistor to the first charge storage region;
   wherein the control circuitry is configured to control the switch to connect the gate terminal of the second transfer transistor to the first charge storage region after a non-visible light collecting period of the electronic device; and
   wherein the second transfer transistor is configured to transfer an amount of charge from the photodiode to the second charge storage region based on the amount of charge in the first charge storage region when the switch connects the gate terminal of the second transfer transistor to the first charge storage region.

10. The electronic device defined in claim 9, further comprising:
   readout circuitry having at least one source follower transistor, wherein the at least one source follower transistor is configured to convert the charges stored on the second charge storage region of a selected one of the time-of-flight image pixels into a depth-image signal and wherein the readout circuitry is configured to read out the depth-image signal.

11. The electronic device defined in claim 10, further comprising:
   processing circuitry configured to extract depth information from the depth-image signal.

12. The electronic device defined in claim 9, further comprising:
   an array of lenses; and
   an array of image sensors, wherein at least one of the image sensors includes the array of time-of-flight image pixels and wherein each lens is configured to focus image light onto a corresponding one of the image sensors.

13. The electronic device defined in claim 12, further comprising:
   processing circuitry, wherein the array of image sensors includes a red image sensor, a blue image sensor, and a green image sensor, wherein the processing circuitry is configured to combine image data from the red image sensor, the blue image sensor, and the green image sensor to form a color image, and wherein the processing circuitry is configured to process depth-image data from the at least one of the image sensors that includes the array of time-of flight image pixels.

* * * * *